United States Patent
Chinta et al.

(10) Patent No.: US 10,022,710 B2
(45) Date of Patent: Jul. 17, 2018

(54) METHOD OF FORMING A CATALYST WITH AN ION-MODIFIED BINDER

(71) Applicant: FINA TECHNOLOGY, INC., Houston, TX (US)

(72) Inventors: Sivadinarayana Chinta, Sugar Land, TX (US); Joseph E. Pelati, Houston, TX (US)

(73) Assignee: FINA TECHNOLOGY, INC., Houston, TX (US)

( * ) Notice: Subject to any disclaimer, the term of this patent is extended or adjusted under 35 U.S.C. 154(b) by 718 days.

(21) Appl. No.: 14/525,456

(22) Filed: Oct. 28, 2014

(65) Prior Publication Data

US 2015/0051063 A1    Feb. 19, 2015

Related U.S. Application Data

(63) Continuation-in-part of application No. 13/113,063, filed on May 22, 2011, now Pat. No. 8,912,109,
(Continued)

(51) Int. Cl.

| | |
|---|---|
| *B01J 29/06* | (2006.01) |
| *B01J 29/068* | (2006.01) |
| *B01J 29/26* | (2006.01) |
| *B01J 29/064* | (2006.01) |
| *B01J 29/076* | (2006.01) |
| *B01J 29/08* | (2006.01) |
| *B01J 29/24* | (2006.01) |
| *B01J 29/14* | (2006.01) |
| *B01J 29/18* | (2006.01) |

(Continued)

(52) U.S. Cl.
CPC ............. *B01J 29/061* (2013.01); *B01J 29/06* (2013.01); *B01J 29/064* (2013.01); *B01J 29/068* (2013.01); *B01J 29/072* (2013.01); *B01J 29/076* (2013.01); *B01J 29/087* (2013.01); *B01J 29/088* (2013.01); *B01J 29/143* (2013.01); *B01J 29/146* (2013.01); *B01J 29/16* (2013.01); *B01J 29/163* (2013.01); *B01J 29/166* (2013.01); *B01J 29/185* (2013.01); *B01J 29/24* (2013.01); *B01J 29/26* (2013.01); *B01J 29/405* (2013.01); *B01J 29/46* (2013.01); *B01J 29/48* (2013.01); *B01J 29/505* (2013.01); *B01J 29/56* (2013.01); *B01J 29/58* (2013.01); *B01J 29/605* (2013.01); *B01J 29/63* (2013.01); *B01J 29/64* (2013.01); *B01J 29/7053* (2013.01); *B01J 29/7057* (2013.01); *B01J 29/7088* (2013.01); *B01J 29/7607* (2013.01); *B01J 29/7615* (2013.01); *B01J 29/7676* (2013.01); *B01J 29/7807* (2013.01); *B01J 29/7815* (2013.01); *B01J 29/7876* (2013.01); *B01J 29/90* (2013.01); *B01J 35/0006* (2013.01); *B01J 37/0009* (2013.01); *B01J 37/0018* (2013.01); *C07C 2/66* (2013.01); *B01J 2229/20* (2013.01); *B01J 2229/24* (2013.01); *B01J 2229/26* (2013.01); *B01J 2229/42* (2013.01); *C07C 2521/04* (2013.01); *C07C 2521/08* (2013.01); *C07C 2523/02* (2013.01); *C07C 2523/06* (2013.01); *C07C 2523/14* (2013.01); *C07C 2523/18* (2013.01); *C07C 2523/22* (2013.01); *C07C 2523/34* (2013.01); *C07C 2523/72* (2013.01); *C07C 2523/745* (2013.01); *C07C 2523/75* (2013.01); *Y02P 20/584* (2015.11); *Y02P 20/588* (2015.11)

(58) Field of Classification Search
CPC ...... B01J 29/061; B01J 29/064; B01J 29/068; B01J 29/072; B01J 29/076; B01J 29/087; B01J 29/088; B01J 29/143; B01J 29/146; B01J 29/16; B01J 29/163; B01J 29/166; B01J 29/185; B01J 29/24; B01J 29/26; B01J 29/405; B01J 29/46; B01J 29/48; B01J 29/505; B01J 29/56; B01J 29/58; B01J 29/605; B01J 29/63; B01J 29/64; B01J 29/7053; B01J 29/29; B01J 29/7057; B01J 29/7088; B01J 29/7607; B01J 29/7615; B01J 29/7676; B01J 29/7807; B01J 29/7815; B01J 29/7876; B01J 37/0009; B01J 37/0018; B01J 35/0006; B01J 2229/42; B01J 2229/20; B01J 2229/24; B01J 2229/26
USPC ... 502/64, 65, 66, 69, 71, 73, 74, 77, 78, 79
See application file for complete search history.

(56) References Cited

U.S. PATENT DOCUMENTS

| | | |
|---|---|---|
| 4,483,937 A | 11/1984 | Liu |
| 6,033,643 A | 3/2000 | Yuen et al. |

(Continued)

OTHER PUBLICATIONS

Extended European Search Report issued in Application No. 12789505.0, dated Jun. 16, 2015, 6 pages.
(Continued)

*Primary Examiner* — Elizabeth D Wood
(74) *Attorney, Agent, or Firm* — Albert Shung

(57) ABSTRACT

An alkylation catalyst having a zeolite catalyst component and a binder component providing mechanical support for the zeolite catalyst component is disclosed. The binder component is an ion-modified binder that can include metal ions selected from the group consisting of Co, Mn, Ti, Zr, V, Nb, K, Cs, Ga, B, P, Rb, Ag, Na, Cu, Mg, Fe, Mo, Ce, and combinations thereof. The metal ions reduce the number of acid sites on the zeolite catalyst component. The metal ions can range from 0.1 to 50 wt % based on the total weight of the ion-modified binder. Optionally, the ion-modified binder is present in amounts ranging from 1 to 80 wt % based on the total weight of the catalyst.

15 Claims, 2 Drawing Sheets

Related U.S. Application Data which is a continuation-in-part of application No. 12/345,593, filed on Dec. 29, 2008, now Pat. No. 8,105,969.

(51) Int. Cl.

| | |
|---|---|
| *B01J 29/46* | (2006.01) |
| *B01J 29/16* | (2006.01) |
| *B01J 29/40* | (2006.01) |
| *B01J 29/48* | (2006.01) |
| *B01J 29/60* | (2006.01) |
| *B01J 29/58* | (2006.01) |
| *B01J 29/56* | (2006.01) |
| *B01J 29/50* | (2006.01) |
| *B01J 29/70* | (2006.01) |
| *B01J 29/64* | (2006.01) |
| *B01J 29/63* | (2006.01) |
| *B01J 29/76* | (2006.01) |
| *B01J 29/78* | (2006.01) |
| *B01J 35/00* | (2006.01) |
| *B01J 29/072* | (2006.01) |
| *B01J 29/90* | (2006.01) |
| *B01J 37/00* | (2006.01) |
| *C07C 2/66* | (2006.01) |

(56) References Cited

U.S. PATENT DOCUMENTS

| | | | |
|---|---|---|---|
| 2004/0111001 A1 | 6/2004 | Dandekar et al. | |
| 2006/0128555 A1* | 6/2006 | Shan | B01J 21/06 502/64 |
| 2010/0076233 A1* | 3/2010 | Cortright | B01J 23/6567 585/251 |
| 2010/0167913 A1 | 7/2010 | Pelati et al. | |
| 2011/0039688 A1* | 2/2011 | Choi | B01J 29/076 502/68 |
| 2012/0296141 A1* | 11/2012 | Chinta | C07C 2/864 585/437 |

OTHER PUBLICATIONS

Chinese Office Action issued in Application No. 201280024806.3, dated Mar. 26, 2015, 20 pages.

\* cited by examiner

METHOD OF FORMING A CATALYST WITH AN ION-MODIFIED BINDER

CROSS-REFERENCE TO RELATED APPLICATIONS

The present application is a divisional of U.S. application Ser. No. 13/113,063, filed on May 22, 2011, which is a continuation-in-part of U.S. application Ser. No. 12/345,593, filed on Dec. 29, 2008.

FIELD

The present invention generally relates to binders used with catalysts such as zeolite, for alkylation and other reactions. More specifically, the present invention relates to alkylation reactions of toluene with methanol and/or formaldehyde utilizing catalysts having binders.

BACKGROUND

A zeolite is a crystalline alumino-silicate catalyst that is well known for its utility in several applications. Zeolites have been used in dealkylation, transalkylation, isomerization, cracking, and disproportionation processes, among others. Its well-ordered structure is composed of tetrahedral $AlO_4^{-4}$ and $SiO_4^{-4}$ molecules bound by oxygen atoms that form a system of pores typically on the order of 3 Å to 10 Å in diameter. These pores create a high internal surface area and allow the zeolite to selectively adsorb certain molecules while excluding others, based on the shape and size of the molecules. Thus, a zeolite can be categorized as a molecular sieve. A zeolite can also be termed a "shape selective catalyst." The small pores of the zeolite can restrict reactions to certain transition states or certain products, preventing shapes that do not fit the contours or dimensions of the pores.

The pores of a zeolite are generally occupied by water molecules and cations. Cations balance out the negative charge caused by trivalent aluminum cations which are coordinated tetrahedrally by oxygen anions. A zeolite can exchange its native cations for other cations; one example is the exchange of sodium ions for ammonium ions. In some ion-exchanged forms, such as the hydrogen form of a zeolite, the catalyst is strongly acidic. The acidic active sites are useful for alkylation as well as many other reactions. For instance, zeolites can serve as a solid acid catalyst for Friedel-Crafts alkylations, replacing traditional aluminum trichloride and other liquid acid catalysts that can be corrosive and damaging to the reactor.

One alkylation reaction for which zeolite can be used as a catalyst is the alkylation of toluene with methanol and/or formaldehyde to form styrene. Styrene, also known as vinyl benzene, is an organic compound having the chemical formula $C_6H_5CHCH_2$. The monomer styrene may be polymerized to form the polymer polystyrene. Polystyrene is a plastic that can form many useful products, including molded products and foamed products, all of which increase the need for production of styrene.

In the production of styrene, zeolite catalysts may be utilized. The zeolite used in the production of styrene can be categorized as a heterogeneous catalyst, because it is in a different phase than the reactants. The zeolite catalyst is solid and usually supported by an alumina or silica binder to increase its mechanical stability inside the reactor bed. The reactants, on the other hand, are either in the liquid, vapor, or supercritical phase. The production of styrene via alkylation has been done with toluene in the gaseous phase, but it is also possible to use liquid phase alkylation, which requires lower temperatures. Liquid phase alkylation can be more economical in certain situations and can decrease the production of unwanted by-products.

Bulk zeolitic catalysts typically contain an abundance of acid sites. In the presence of alkylation reactions, these acid sites as well as the overall shape selectivity of a typical alkylation zeolite catalyst may contribute to the production of unwanted by-products, such as xylenes.

Therefore, it would be desirable to reduce the amount of the acid sites on a zeolitic catalyst used in the production of styrene. It would also be desirable to use an alkylation catalyst capable of increasing the selectivity to styrene.

SUMMARY

The present invention in its many embodiments relates to a catalyst for making styrene by the alkylation of toluene. An embodiment of the present invention includes an alkylation catalyst having a catalyst component and a binder component providing mechanical support for the zeolite catalyst component. The binder component in this embodiment is an ion-modified binder including metal ions selected from the group consisting of Co, Mn, Ti, Zr, V, Nb, K, Cs, Ga, B, P, Rb, Ag, Na, Cu, Mg, Fe, Mo, Ce, and combinations thereof. The metal ions reduce the number of acid sites on the zeolite catalyst component. The metal ions can range from 0.1 to 50 wt % based on the total weight of the ion-modified binder. The ion-modified binder can be present in amounts ranging from 1 to 80 wt % based on the total weight of the catalyst.

In an embodiment the metal ions on the ion-modified binder can alter the spacial structure of the catalyst. The binder can include amorphous silica or alumina. The catalyst can be a molecular sieve catalyst, and can be a zeolite. In an embodiment Cs can be present in the binder in the form of cesium silicate.

In an embodiment, a process for making styrene by the alkylation of toluene includes providing toluene and a C1 source to one or more reactors and reacting the toluene with the C1 source in the one or more reactors to form a product stream including ethylbenzene and styrene. The C1 source can be selected from the group consisting of methanol and formaldehyde and combinations thereof. In this process, at least one of the one or more reactors includes a catalyst component including a binder component providing mechanical support for the catalyst component, wherein the binder component reduces the number of acid sites on the catalyst. The binder component can include amorphous silica or alumina. Optionally, cesium is present in the binder in the form of cesium silicate.

In an embodiment, either by itself or in combination with any other embodiment, the binder component is an ion-modified binder. The ion-modified binder can alter the shape selectivity of the catalyst resulting in an increase of product selectivity as compared to the use a non ion-modified binder. The ion-modified binder can include metal ions in amounts ranging from 0.1 to 50 wt % based on the total weight of the ion-modified binder. Optionally, the ion-modified binder includes metal ions in amounts ranging from 0.1 to 20 wt % based on the total weight of the ion-modified binder. The metal ions can be selected from the group consisting of Co, Mn, Ti, Zr, V, Nb, K, Cs, Ga, B, P, Rb, Ag, Na, Cu, Mg, Fe, Mo, Ce, and combinations thereof.

In an embodiment, either by itself or in combination with any other embodiment, the ion-modified binder is present in the catalyst in amounts ranging from 1 to 80 wt % based on the total weight of the catalyst. Optionally, the ion-modified binder is present in the catalyst in amounts ranging from 5 to 60 wt % based on the total weight of the catalyst. Optionally, the catalyst is a molecular sieve catalyst. In a nonlimiting embodiment, the catalyst is a zeolite.

In yet another embodiment of the present invention, a method for preparing a zeolite alkylation catalyst includes adding metal ions to a binder via incipient wetness to form an ion-modified binder and combining the ion-modified binder with a zeolite to form a zeolite aggregate. The zeolite aggregate is further processed to form a zeolite alkylation catalyst. The zeolite alkylation catalyst can be used in a reaction bed for the alkylation of toluene with a methanol. In this embodiment, the ion-modified binder reduces the number of acid sites on the zeolite and metal ions on the ion-modified binder alter the spacial structure of the zeolite. The metal ions can be selected from the group consisting of Ce, Cu, P, Cs, B, Co, Ga, and combinations thereof, and in an embodiment the ion-modified binder can include cesium silicate and alter the shape selectivity of the zeolite.

Other possible embodiments include two or more of the above embodiments of the invention. In an embodiment the method includes all of the above embodiments and the various procedures can be carried out in any order.

DETAILED DESCRIPTION

Figure 1:
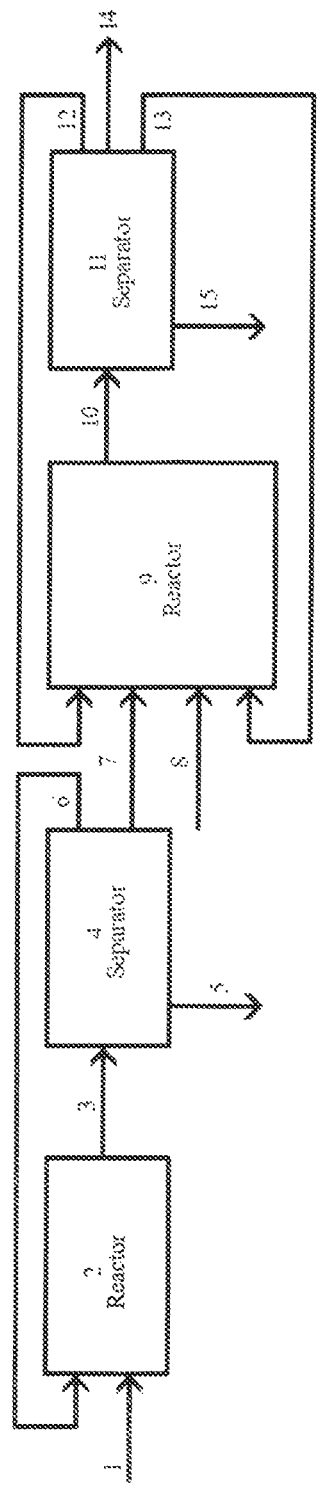
FIG. 1 illustrates a flow chart for the production of styrene by the reaction of formaldehyde and toluene, wherein the formaldehyde is first produced in a separate reactor by either the dehydrogenation or oxidation of methanol and is then reacted with toluene to produce styrene.

The present invention relates to increasing the selectivity in an alkylation process, specifically an alkylation of toluene with methanol (ATM) process. More specifically, the present invention is related to the modification of a binder for a catalyst, such as a zeolite catalyst, to reduce the number of acid sites on the catalyst. Also, the binder can be modified by the addition of active metal species in a way that may change the shape selectivity of the zeolite catalyst, such that by-product formation is inhibited and styrene selectivity is increased. Also, the present invention includes the optimization of binder content in the catalyst formation such that the activity and selectivity of the catalyst may be increased.

The powder form of a zeolite and other catalysts may be unsuitable for use in a reactor, due to a lack of mechanical stability, making alkylation and other desired reactions difficult. To render a catalyst suitable for the reactor, the zeolite catalyst component can be combined with a binder to form an aggregate, such as a zeolite aggregate. The binder-modified zeolite, such as a zeolite aggregate, will have enhanced mechanical stability and strength over a zeolite that is not combined with a binder, or otherwise in powder form. The aggregate can then be processed, such as shaped or extruded, into a form suitable for the reaction bed. The binder can desirably withstand temperature and mechanical stress and ideally does not interfere with the reactants adsorbing to the catalyst. The binder may form macropores, much greater in size than the pores of the catalyst, which provide improved diffusional access of the reactants to the catalyst.

Binder materials that are suitable for the present invention include, but are not limited to, silica, alumina, titania, zirconia, zinc oxide, magnesia, boria, silica-alumina, silica-magnesia, chromia-alumina, alumina-boria, silica-zirconia, silica gel, clays, kaolin, montmorillonite, modified clays, similar species, and any combinations thereof. The most frequently used binders are amorphous silica and alumina, including gamma-, eta-, and theta-alumina. It should be noted that a binder can be used with many different catalysts, including various forms of zeolite and non-zeolite catalysts that require mechanical support.

According to the present invention, the binder is modified such that it provides mechanical support and performs other typical functions of a binder, as well as reducing the number of acid sites on the catalyst. Also according to the present invention, the binder is modified by the addition of a metal such that it alters the shape selectivity of the catalyst. The binder of the present invention may be composed of alumina or silica or similar amorphous material and includes metal ions or similar species. The active metal ions may be ions of the following non-limiting examples of Co, Mn, Ti, Zr, V, Nb, K, Cs, Ga, B, P, Rb, Ag, Na, Cu, Mg, Fe, Mo, Ce, or similar species such as metal oxides, nanoparticles, or mixed metal oxide phases. In another embodiment, the active metal ions may include ions selected from the group of Ce, Cu, P, Cs, B, Co, Ga, or combinations thereof. Other similar metal ions and species not listed may be used, as well as combinations of any of the listed and unlisted metal ions and similar species.

As used herein, the term "metal ion" is meant to include all active metal ions and similar species, such as metal oxides, nanoparticles, and mixed metal oxide phases, capable of being added to a binder and enabling the binder to reduce the acidity, or increase the basicity or basic strength, of the supported catalyst without adversely affecting the catalyst that it supports or causing significant by-product formation at reaction conditions. Further, the term "ion-modified binder" as used herein refers to a binder for a catalyst that has been modified with a metal ion.

The metal ion can be added to the binder in the amount of 0.1% to 50%, optionally 0.1% to 20%, optionally 0.1% to 5%, by weight of the binder. The metal ion can be added to the binder by any means known in the art. One method that can be used is incipient wetness impregnation, wherein the metal ion precursor is added to an aqueous solution, which solution is poured over the binder. After sitting for a specified period, the binder is dried and calcined, such that the water is removed with the metal ion deposited on the binder surface. The ion-modified binder can then be mixed with a catalyst by any means known in the art, such as by compounding, slurry mixing, etc. The mixture can be shaped via extrusion or some other method into a form such as a pellet, tablet, cylinder, cloverleaf, dumbbell, symmetrical and asymmetrical polylobates, sphere, or any other shape suitable for the reaction bed. The shaped form is then usually dried and calcined. Drying can take place at a temperature of from 100° C. to 200° C. Calcining can take place at a temperature of from 400° C. to 1000° C. in a substantially dry environment. The resultant catalyst aggregate can contain ion-modified binder in concentrations of from 1% to 80%, optionally from 5% to 50%, optionally from 10% to 30%, by weight of the catalyst aggregate. The percent weight of the catalyst that is binder can be altered depending on the temperature of the reaction zone in which the catalyst will be used. Generally the binder can withstand higher temperatures and a higher percentage of binder can be added for a higher temperature application. For example, in the use of zeolite for an alkylation reaction, about 50% zeolite and 50% binder can be used in the higher temperature alkylation catalyst beds and about 75% zeolite and 25% binder can be used in the lower temperature alkylation catalyst beds.

In a specific embodiment, a cesium promoter may be combined with a binder in the form of cesium silicate such as $Cs_6Si_{10}O_{23}$. Cesium silicate crystals may be prepared upon the crystallization of glass $Cs_2O.4SiO_2$. The crystals of cesium silicate may act to create a confined space in the catalysts, such that the catalytically active sites are selectively accessible to the desired reactants. In an embodiment, the cesium is added to the silica portion of a silica-alumina material, resulting in a cesium silicate portion attached to the silica-alumina material. The cesium silicate is a large molecule, which when added to the silica portion, creates cavities that can contain the catalytically active site(s). These cavities are confined spaces in which toluene and a $C_1$ source can enter, react, and then leave. These cavities can alter the selectivity of the process resulting in an increase in product selectivity.

For the present invention, the catalyst to be supported and protected by the ion-modified binder can be a zeolite, but can also be a non-zeolite. A zeolite is generally a porous, crystalline alumino-silicate, and it can be formed either naturally or synthetically. One method of forming a synthetic zeolite is the hydrothermal digestion of silica, alumina, sodium or other alkyl metal oxide, and an organic templating agent. The amounts of each reactant and the inclusion of various metal oxides can lead to several different synthetic zeolite compositions. Furthermore, a zeolite is commonly altered through a variety of methods to adjust characteristics such as pore size, structure, activity, acidity, and silica/alumina molar ratio. Thus, a number of different forms of zeolite are available. As used herein a zeolite catalyst component can refer to the zeolite or non-zeolite composition as opposed to the binder component. The zeolite catalyst component can refer to the zeolite or non-zeolite composition prior to the addition of the binder component to form the aggregate, such as a zeolite aggregate.

Zeolite materials suitable for this invention may include silicate-based zeolites and amorphous compounds such as faujasite, mordenite, chabazite, offretite, clinoptilolite, erionite, sihealite, and the like. Silicate-based zeolites are made of alternating $SiO_2$ and $MO_x$ tetrahedra, where M is an element selected from the Groups 1 through 16 of the Periodic Table (new IUPAC). These types of zeolites have 4-, 6-, 8-, 10-, or 12-membered oxygen ring channels. An example of zeolites of this invention can include faujasites. Other suitable zeolite materials include zeolite A, zeolite L, zeolite beta, zeolite X, zeolite Y, ZSM-5, MCM-22, and MCM-41. In a more specific embodiment, the zeolite is an X-type zeolite. Alternate molecular sieves also contemplated are zeolite-like materials such as the crystalline silicoaluminophosphates (SAPO) and the aluminophosphates (ALPO).

Another method of altering a zeolite is by ion-exchange. For example, the hydrogen form of a zeolite can be produced by ion-exchanging beta zeolite with ammonium ions. Metal ions can also be incorporated into a zeolite, either by ion-exchange or another method. Further, the silica/alumina ratio of the zeolite can be altered, via a variety of methods, such as dealumination by steaming or acid washing to increase the silica/alumina ratio. Increasing the amount of silica relative to alumina can have the effect of increasing the catalyst hydrophobicity. The silica/alumina ratio can range from less than 0.5 to 500 or greater. Some catalysts other than zeolitic catalysts can also be used with a binder of the present invention, including catalysts that fall into the general categories of molecular sieves and/or solid acid catalysts.

Thus, a variety of zeolites and non-zeolites are available for use in conjunction with the ion-modified binder of the present invention. The various catalysts listed in the two preceding paragraphs are not meant to be an exhaustive list, but is meant to indicate the type of catalysts for which an ion-modified binder can be useful. The choice of catalyst will depend on the reaction type and the reaction conditions in which it will be used. One skilled in the art can select any zeolite or non-zeolite catalyst that meets the needs of the intended reaction, provided that an ion-modified binder can be used to support the catalyst and either reduce the number of acid sites on the catalyst and/or alter the shape selectivity of the catalyst to improve product selectivity.

Once the catalyst becomes supported by the ion-modified binder, the metal ions of the ion-modified binder may attach to the catalytically active acid sites of the catalyst, thus reducing the acidity or the total number of acid sites of the catalyst. Upon attachment of the metal ions with the acid sites of the catalyst, the structural dimensions of the catalyst may also be changed. The changed structural dimensions of the catalyst may result in the catalyst having an altered shape selectivity. In an embodiment, once the catalyst becomes supported by the ion-modified binder, the metal ions of the ion-modified binder may attach to the catalytically active acid sites of the catalyst, thus changing the structural dimensions of the catalyst, which may result in the catalyst having an altered shape selectivity.

An improvement in side chain alkylation selectivity may be achieved by treating a molecular sieve zeolite catalyst with chemical compounds to inhibit the external acidic sites and minimize aromatic alkylation on the ring positions. Another means of improvement of side chain alkylation selectivity can be to impose restrictions on the catalyst structure to facilitate side chain alkylation. In one embodiment the catalyst used in an embodiment of the present invention is a basic or neutral catalyst.

The catalytic reaction systems suitable for this invention can include one or more of the zeolite or amorphous materials modified for side chain alkylation selectivity. A non-limiting example can be a zeolite promoted with one or more of the following: Co, Mn, Ti, Zr, V, Nb, K, Cs, Ga, B, P, Rb, Ag, Na, Cu, Mg, Fe, Mo, Ce, or combinations thereof. In an embodiment, the zeolite can be promoted with one or more of Ce, Cu, P, Cs, B, Co, Ga, or combinations thereof. In general the promoter exchanges with Na within the zeolite. The promoter can also be attached to the zeolite in an occluded manner. In an embodiment the amount of promoter is determined by the amount needed to yield less than 0.5 mol % of ring alkylated products such as xylenes from a coupling reaction of toluene and a $C_1$ source.

In an embodiment, the catalyst contains greater than 0.1 wt % of at least one promoter based on the total weight of the catalyst. In another embodiment, the catalyst contains up to 5 wt % of at least one promoter. In a further embodiment, the catalyst contains from 1 to 3 wt % of at least one promoter.

Processes for which an ion-modified binder can be used include, but are not limited to, oxidation, reduction, adsorption, dimerization, oligomerization, polymerization, etherification, esterification, hydration, dehydration, condensation, acetalization, dealkylation, cyclization, alkylation, dehydrogenation, hydrodealkylation, transalkylation, isomerization, cracking, disproportionation, hydroisomerization, hydrocracking, aromatization, and any process employing a molecular sieve catalyst in which the total amount of acid sites is wished to be reduced. In an embodiment, the ion-modified binder is used in an alkylation and dehydrogenation process.

Many different forms of alkylation reactions are possible. In general, alkylation occurs when an alkylating agent consisting of one or more carbon atoms is added to an alkylatable substrate. Alkylating agents that can be used in alkylation reactions are generally olefins. An olefin can be short chain, like ethylene, propylene, butene, and pentene, or it can be long chain with a higher number of carbon atoms. It can be an alpha olefin, an isomerized olefin, a branched-chain olefin or a mixture thereof. Alkylating agents other than olefins include alkynes, alkyl halides, alcohols, ethers, and esters. In some cases, the alkylating agent is diluted with a diluting agent prior to its introduction into the reaction bed. Especially for ethylene, diluting agents such as inert, or nonreactive, gases like nitrogen can be used. In an embodiment the concentration of the diluting agent can be greater than the concentration of the alkylating agent in the diluted feedstream, such as around 70% diluting agent and 30% alkylating agent.

The alkylatable substrate is usually an unsaturated hydrocarbon or an aromatic. If the alkylatable substrate is an aromatic compound, it can be unsubstituted, monosubstituted, or polysubstituted, and it possesses at least one hydrogen atom bonded directly to the aromatic nucleus or some other site that will allow for alkylation to occur. The aromatic nucleus can be benzene or a compound comprising more than one aromatic ring, like naphthalene, anthracene, naphthacene, perylene, coronene, and phenanthrene. Compounds that have an aromatic character but contain a heteroatom in the ring can also be used, provided they will not cause unwanted side reactions. Substituents on the aromatic nucleus can be alkyl, hydroxy, alkoxy, aryl, alkaryl, aryloxy, cycloalkyl, halide, and/or other groups which do not interfere with the alkylation reaction and that comprise 1 to 20 carbon atoms. Aromatic substrates that may be alkylated by an alkylating agent include benzene, toluene, xylene, biphenyl, ethylbenzene, isopropylbenzene, normal propylbenzene, butylbenzene, pentylbenzene, hexylbenzene, heptylbenzene, octylbenzene, nonylbenzene, dodecylbenzene, pentadecylbenzene, hexyltoluene, nonyltoluene, dodecyltoluene, pentadecyltoluene, alpha-methylnaphthalene, mesitylene, durene, cymene, pseudocumene, diethylbenzene, isoamylbenzene, isohexylbenzene, pentaethylbenzene, pentamethylbenzene, tetraethylbenzene, tetramethylbenzene, triethylbenzene, trimethylbenzene, butyltoluene, diethyltoluene, ethyltoluene, propyltoluene, dimethylnaphthalenes, ethylnaphthalene, dimethylanthracene, ethylanthracene, methylanthracene, dimethylphenanthrene, phenanthrenephenol, cresol, anisole, ethoxybenzene, propoxybenzene, butoxybenzene, pentoxybenzene, hexoxybenzene, any isomers thereof, and the like. In an embodiment, the aromatic substrate to be alkylated is toluene. In another embodiment, the alkylation reaction of the present invention includes the alkylation of toluene with methanol and/or formaldehyde.

Reactants for the alkylation of toluene generally include methanol as the alkylating agent and toluene as the alkylatable substrate. In general, toluene is reacted with a $C_1$ source to produce styrene and ethylbenzene. The $C_1$ source may include methanol or formaldehyde or a mixture of the two. Alternatively, toluene may be reacted with one or more of the following: formalin, trioxane, methylformcel, paraformaldehyde, methylal and dimethyl ether. In another embodiment, the $C_1$ source is selected from the group consisting of methanol, formaldehyde, Formalin (37-50% $H_2CO$ in solution of water and MeOH), Trioxane (1,3,5-trioxane), Methylformcel (55% $H_2CO$ in methanol), Paraformaldehyde and Methylal (dimethoxymethane), and combinations thereof.

Although the reaction has a 1:1 molar ratio of toluene and the $C_1$ source, the ratio of the feedstreams is not limited within the present invention and can vary depending on operating conditions and the efficiency of the reaction system. If excess toluene or $C_1$ source is fed to the reaction zone, the unreacted portion can be subsequently separated and recycled back into the process. In one embodiment the ratio of toluene:$C_1$ source can range from between 100:1 to 1:100. In alternate embodiments the ratio of toluene:$C_1$ source can range between from 50:1 to 1:50; from 20:1 to 1:20; from 10:1 to 1:10; from 5:1 to 1:5; and from 2:1 to 1:2.

The operating conditions of the reactors and separators will be system specific and can vary depending on the feedstream composition and the composition of the product streams. The reactor for the reactions of methanol to formaldehyde and toluene with formaldehyde will operate at elevated temperatures. The temperature can range in a non-limiting example from 250° C. to 750° C., optionally from 300° C. to 500° C., optionally from 375° C. to 450° C. The pressure can range in a non-limiting example from 0.1 atm to 70 atm, optionally from 0.1 atm to 35 atm, optionally from 0.1 atm to 10 atm, optionally from 0.1 atm to 5 atm.

In FIG. 1 there is a simplified flow chart of one embodiment of the styrene production process described above. In this embodiment, a first reactor (2) is either a dehydrogenation reactor or an oxidation reactor. In an embodiment this reactor is designed to convert the first methanol feed (1) into formaldehyde. The gas product (3) of the reactor is then sent to a gas separation unit (4) where the formaldehyde is separated from any unreacted methanol and unwanted byproducts. Any unreacted methanol (6) can then be recycled back into the first reactor (2). The byproducts (5) are separated from the clean formaldehyde (7).

In one embodiment the first reactor (2) is a dehydrogenation reactor that produces formaldehyde and hydrogen and the separation unit (4) is a membrane capable of removing hydrogen from the product stream (3).

In an alternate embodiment the first reactor (2) is an oxidative reactor that produces product stream (3) comprising formaldehyde and water. The product stream (3) comprising formaldehyde and water can then be sent to the second reactor (9) without a separation unit (4).

The formaldehyde feed stream (7) is then reacted with a feed stream of toluene (8) in a second reactor (9). The toluene and formaldehyde react to produce styrene. The product (10) of the second reactor (9) may then be sent to an optional separation unit (11) where any unwanted byproducts (15) such as water can be separated from the styrene, unreacted formaldehyde and unreacted toluene. Any unreacted formaldehyde (12) and the unreacted toluene (13) can be recycled back into the reactor (9). A styrene product stream (14) can be removed from the separation unit (11) and subjected to further treatment or processing if desired.

The operating conditions of the reactors and separators will be system specific and can vary depending on the feedstream composition and the composition of the product streams. The reactor (9) for the reaction of toluene and formaldehyde will operate at elevated temperatures, such as for a non-limiting example from 250° C. to 750° C. and from 0.1 atm to 70 atm in pressure and may contain a basic or neutral catalyst system.

Figure 2:
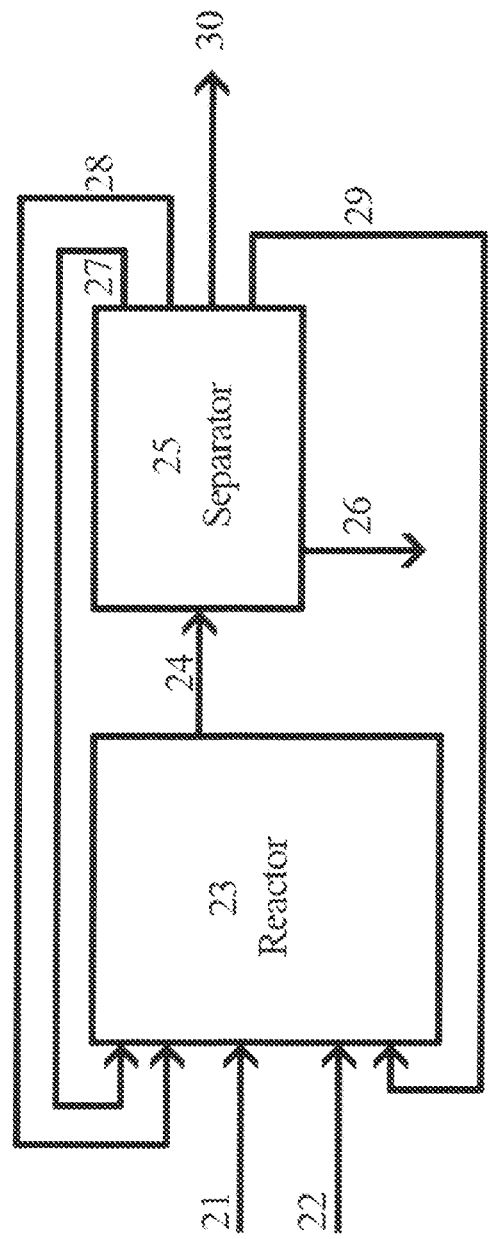
FIG. 2 illustrates a flow chart for the production of styrene by the reaction of formaldehyde and toluene, wherein methanol and toluene are fed into a reactor, wherein the methanol is converted to formaldehyde and the formaldehyde is reacted with toluene to produce styrene.

FIG. 2 is a simplified flow chart of another embodiment of the styrene process discussed above. A methanol containing feed stream (21) is fed along with a feed stream of toluene (22) in a reactor (23). The methanol reacts with a catalyst in the reactor to produce formaldehyde. The toluene and formaldehyde then react to produce styrene. The product (24) of the reactor (23) may then be sent to an optional separation unit (25) where any unwanted byproducts (26) can separated from the styrene, unreacted methanol, unreacted formaldehyde and unreacted toluene. Any unreacted methanol (27), unreacted formaldehyde (28) and the unreacted toluene (29) can be recycled back into the reactor (23). A styrene product stream (30) can be removed from the separation unit (25) and subjected to further treatment or processing if desired.

The operating conditions of the reactors and separators will be system specific and can vary depending on the feedstream composition and the composition of the product streams. The reactor (23) for the reactions of methanol to formaldehyde and toluene with formaldehyde will operate at elevated temperatures, such as for a non-limiting example from 250° C. to 750° C. and from 0.1 atm to 70 atm in pressure and may contain a basic or neutral catalyst system.

Zeolite deactivation generally requires a regeneration procedure to be performed. Some methods of regenerating zeolite include heating to remove adsorbed materials, ion exchanging with sodium to remove unwanted cations, or pressure swing to remove adsorbed gases. A regeneration procedure can involve processing the catalyst at high temperatures using regeneration gas and oxygen. According to one procedure, a zeolite beta can be regenerated by heating the catalyst first to a temperature in excess of 300° C. in an oxygen-free environment. Then an oxidative regeneration gas can be supplied to the catalyst bed with oxidation of a portion of a relatively porous coke component to produce an exotherm moving through the catalyst bed. Either the temperature or the oxygen content of the gas can be progressively increased to oxidize a porous component of the coke. Again, regeneration gas can be supplied, wherein the gas has either increased oxygen content or increased temperature to oxidize a less porous refractory component of the coke. The regeneration process can be completed by passing an inert gas through the catalyst bed at a reduced temperature.

The term "ion-modified binder" as used herein refers to a binder for a catalyst that has been modified with a metal ion.

The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

The term "regenerated catalyst" refers to a catalyst that has regained enough activity to be efficient in a specified process. Such efficiency is determined by individual process parameters.

The term "regeneration" refers to a process for renewing catalyst activity and/or making a catalyst reusable after its activity has reached an unacceptable/inefficient level. Examples of such regeneration may include passing steam over a catalyst bed or burning off carbon residue, for example.

The term "zeolite" refers to a molecular sieve containing a silicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

The various embodiments of the present invention can be joined in combination with other embodiments of the invention and the listed embodiments herein are not meant to limit the invention. All combinations of various embodiments of the invention are enabled, even if not given in a particular example herein.

While illustrative embodiments have been depicted and described, modifications thereof can be made by one skilled in the art without departing from the spirit and scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Also, it is within the scope of this disclosure that the embodiments disclosed herein are usable and combinable with every other embodiment disclosed herein, and consequently, this disclosure is enabling for any and all combinations of the embodiments disclosed herein. Other and further embodiments, versions and examples of the invention may be devised without departing from the basic scope thereof and the scope thereof is determined by the claims that follow.

What is claimed:

1. A method for preparing a zeolite alkylation catalyst, comprising:
    adding metal ions to a binder to form an ion-modified binder;
    combining said ion-modified binder with a zeolite to form a zeolite aggregate, wherein the zeolite comprises faujasite, mordenite, chabazite, offretite, clinoptilolite, erionite, or sihealite; and
    processing the zeolite aggregate to form a zeolite alkylation catalyst;
    wherein the ion-modified binder reduces a number of acid sites on the zeolite alkylation catalyst; and
    wherein the metal ions on the ion-modified binder alter structural dimensions of the zeolite alkylation catalyst.

2. The method of claim 1, wherein the metal ions are selected from the group consisting of Ce, Cu, P, Cs, B, Co, Ga, and combinations thereof.

3. The method of claim 1, wherein the ion-modified binder comprises cesium silicate, and wherein the ion-modified binder alters the shape selectivity of the zeolite alkylation catalyst.

4. The method of claim 1, wherein the metal ions are selected from the group consisting of Mn, K, Cs, Ga, Rb, Ag, Na, Cu, Mg, and combinations thereof.

5. The method of claim 1, wherein the metal ions are added to the binder by incipient wetness.

6. The method of claim 1, wherein the metal ions are added to the binder by:
adding a metal ion precursor to an aqueous solution;
pouring the aqueous solution over the binder; and
drying and calcining the binder to remove water, wherein the metal ions are deposited on a surface of the binder.

7. The method of claim 5, wherein combining said ion-modified binder with the zeolite comprises mixing the ion-modified binder with the zeolite, shaping the mixture, and drying and calcining the shaped mixture.

8. The method of claim 1, wherein the metal ions comprise a cesium promoter that is combined with the binder in the form of cesium silicate.

9. The method of claim 8, wherein the cesium silicate is $Cs_6Si_{10}O_{23}$.

10. The method of claim 8, wherein the cesium silicate comprises is in the form of crystals that are prepared upon crystallization of $Cs_2O_4SiO_2$.

11. The method of claim 8, wherein the binder is a silica-alumina material, and wherein crystals of the cesium silicate are added to a silica portion of the silica-alumina material.

12. A method for preparing a zeolite alkylation catalyst, comprising:
adding metal ions to a binder to form an ion-modified binder;
combining said ion-modified binder with a zeolite to form a zeolite aggregate, wherein the zeolite comprises zeolite A, zeolite L, zeolite beta, zeolite X, zeolite Y, ZSM-5, MCM-22, or MCM-41; and
processing the zeolite aggregate to form a zeolite alkylation catalyst;
wherein the ion-modified binder reduces a number of acid sites on the zeolite alkylation catalyst; and
wherein the metal ions on the ion-modified binder alter structural dimensions of the zeolite alkylation catalyst.

13. The method of claim 12, wherein the metal ions are selected from the group consisting of Mn, K, Cs, Ga, Rb, Ag, Na, Cu, Mg, and combinations thereof.

14. The method of claim 12, wherein the metal ions are added to the binder by incipient wetness.

15. The method of claim 12, wherein the metal ions comprise a cesium promoter that is combined with the binder in the form of cesium silicate.

* * * * *